United States Patent [19]

Helwig et al.

[11] Patent Number: 4,769,457

[45] Date of Patent: Sep. 6, 1988

[54] GLYCOLURIL DERIVATIVES AND THEIR USE AS STABILIZERS FOR POLYMERS

[75] Inventors: Reinhard Helwig; Alexander Aumueller, both of Ludwigshafen; Peter Neumann, Wiesloch; Hubert Trauth, Dudenhofen, all of Fed. Rep. of Germany

[73] Assignee: BASF Aktiengesellschaft, Rheinland-Pfalz, Fed. Rep. of Germany

[21] Appl. No.: 895,934

[22] Filed: Aug. 13, 1986

[30] Foreign Application Priority Data

Aug. 28, 1985 [DE] Fed. Rep. of Germany ....... 3530666

[51] Int. Cl.⁴ .......................................... C07D 251/00
[52] U.S. Cl. ..................................... 544/180; 544/215
[58] Field of Search ................................ 544/180, 215

[56] References Cited

FOREIGN PATENT DOCUMENTS 7437838 11/1974 France ............................. 544/215
2107707 9/1982 United Kingdom ................ 544/180

Primary Examiner—Mary C. Lee
Assistant Examiner—J. Richter
Attorney, Agent, or Firm—Oblon, Fisher, Spivak, McClelland & Maier

[57] ABSTRACT

The novel compounds of the general formula I

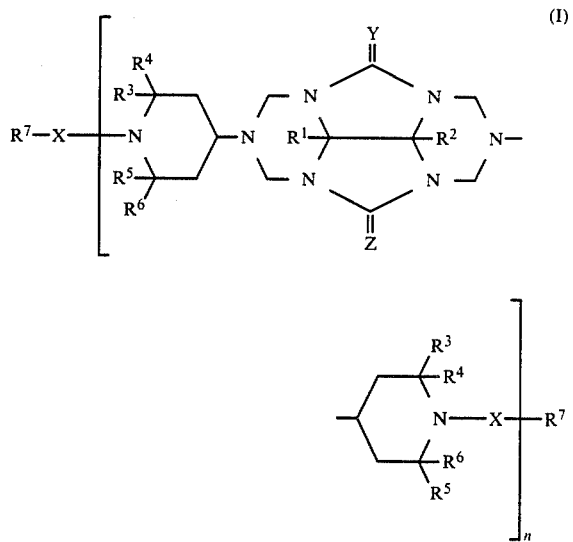

where
n is from 1 to 70,
$R^1$ and $R^2$ independently of one another are each hydrogen, $C_1$–$C_6$-alkyl, $C_7$–$C_{12}$-aralkyl, aryl or a carboxylic ester group, or
$R^1$ and $R^2$ together may form a tetramethylene or pentamethylene group,
$R^3$, $R^4$, $R^5$ and $R^6$ are each alkyl, the radicals
X independently of one another are each a direct bond or a bridge member,
Y and Z are each oxygen, sulfur or $NR^8$,
$R^7$ is hydrogen, chlorine, bromine, hydroxyl, alkoxy, carboxyl, a carboxylic ester group or unsubstituted or substituted carbamyl and $R^8$ is hydrogen or unsubstituted or substituted alkyl, and the ammonium salts of these compounds, are very useful as light stabilizers.

15 Claims, No Drawings

GLYCOLURIL DERIVATIVES AND THEIR USE AS STABILIZERS FOR POLYMERS 2,2,6,6-Tetraalkylpiperidine derivatives are known to be light stabilizers for organic polymers. The compatibility with polyolefins, the duration of the protective action, these tendency to be volatile and the natural color of the substances are often unsatisfactory.

The present invention relates to novel compounds of the general formula (I)

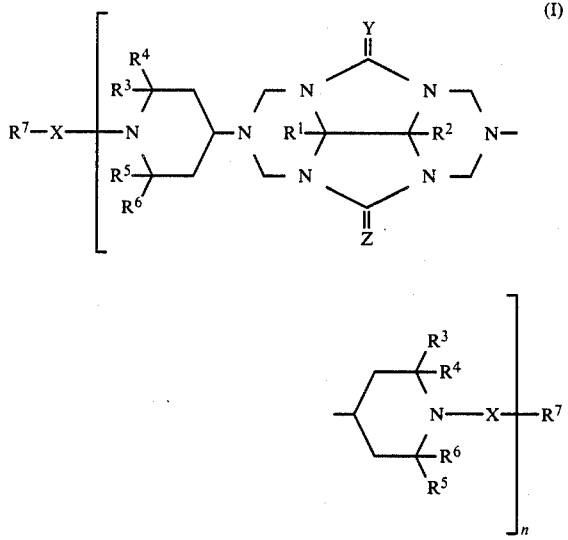

where
n is from 1 to 70,
$R^1$ and $R^2$ independently of one another are each hydrogen, $C_1$–$C_6$-alkyl, $C_7$–$C_{12}$-aralkyl, aryl or a carboxylic ester group, or
$R^1$ and $R^2$ together may form a tetramethylene or pentamethylene group,
$R^3$, $R^4$, $R^5$ and $R^6$ are each alkyl, the radicals
X independently of one another are each a direct bond or a bridge member,
Y and Z are each oxygen, sulfur or $NR^8$,
$R^7$ is hydrogen, chlorine, bromine, hydroxyl, alkoxy, carboxyl, a carboxylic ester group or unsubstituted or substituted carbamyl and $R^8$ is hydrogen or unsubstituted or substituted alkyl, and the ammonium salts of these compounds.

Preferred compounds are those in which n is 1 to 20, in particular 1.

Specific examples of $R^1$ and $R^2$ in addition to hydrogen are methyl, ethyl, propyl, butyl, pentyl, hexyl, benzyl, phenylethyl, phenylpropyl, phenylbutyl, methylbenzyl, phenyl, tolyl, carbomethoxy, carboethoxy, carbopropoxy and carbobutoxy.

$R^1$ and $R^2$ are each preferably ethyl, benzyl, carbomethoxy or carboethoxy, in particular hydrogen, methyl or phenyl.

Examples of alkyl radicals $R^3$, $R^4$, $R^5$ and $R^6$ are $C_1$–$C_4$-alkyl, ie. methyl, ethyl, propyl or butyl. Two adjacent radicals may furthermore form a tetramethylene or pentamethylene group.

$R^3$, $R^4$, $R^5$ and $R^6$ are each preferably methyl.

Bridging members X are divalent aliphatic or araliphatic groups which may contain oxygen, nitrogen or sulfur as heteroatoms or possess double or triple bonds.

Particular examples are alkylene, cycloalkylene, aralkylene, arylene, alkylene, aralkylene or aryl radicals which are substituted by CO or $SO_2$, and alkenylene and alkynylene, each of which may furthermore be interrupted by the stated heteroatoms.

Specific examples of bridge members are:
$(CH_2)_p$, $(CH_2)_p CH=CH$, $(CH_2)_p C\equiv C$,

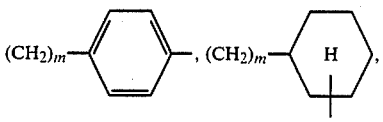

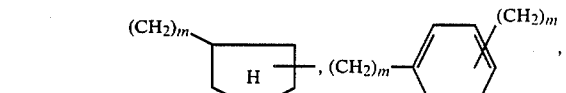

$(CH_2)_2O$, $(CH_2)_2O(CH_2)_2$, $(CH_2)_3O(CH_2)_2$,

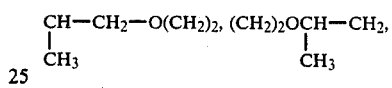

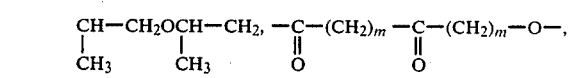

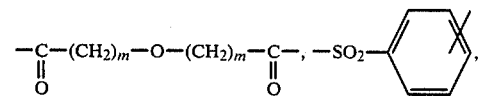

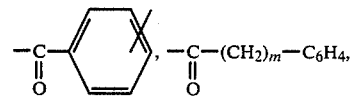

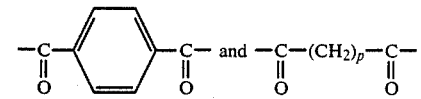

where p is from 1 to 20 and m is from 0 to 4.

Examples of preferred bridging members are:
—$(CH_2)_2$—, —$(CH_2)_3$—, —$(CH_2)_4$—, —$(CH_2)_5$—,
—$(CH_2)_6$—, —$(CH_2)_7$—, —$(CH_2)_8$—, —$(CH_2)_9$—,
—$(CH_2)_{10}$—, —$(CH_2)_{11}$—, —$(CH_2)_{12}$—, —$(CH_2)_{13}$—,
—$(CH_2)_{14}$—, —$(CH_2)_{16}$—, —$(CH_2)_{17}$—, —$(CH_2)_{20}$—, —$CH_2$—CH—$(CH_2)_4$—, —CH—$CH_3$, —$CH_2$—CH=CH—,
      |        |
     $C_2H_5$     $CH_3$

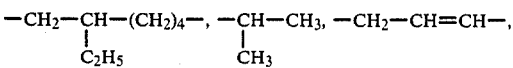

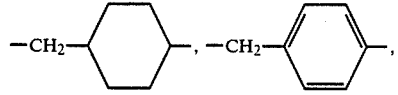

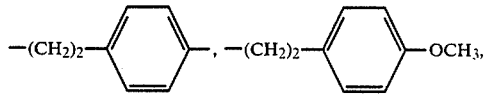

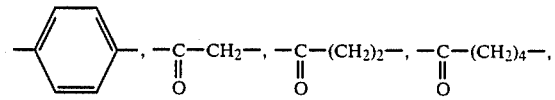

-continued

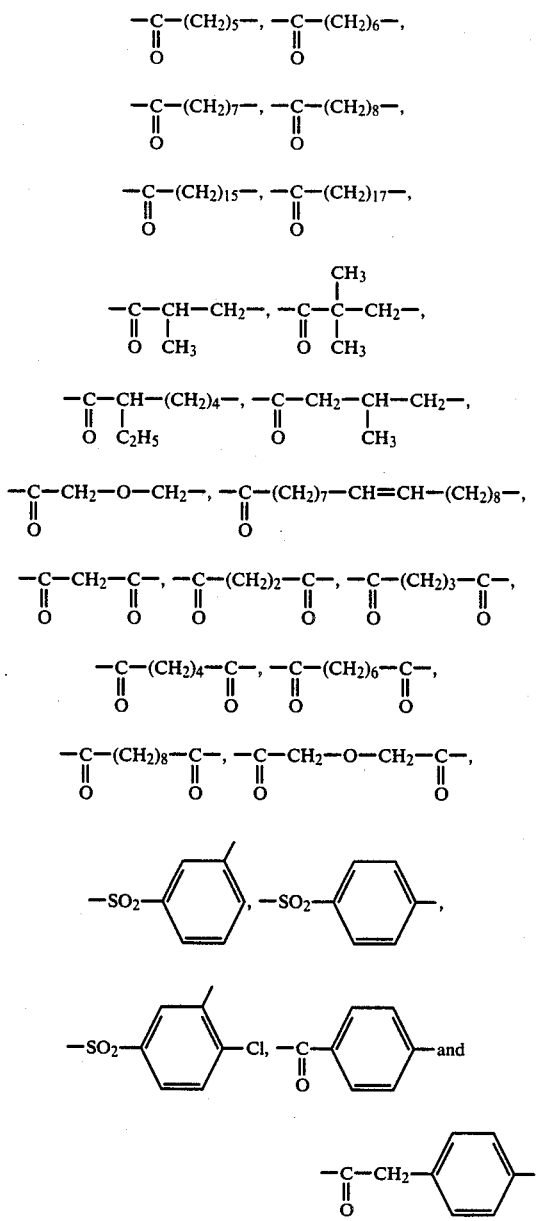

and in particular the direct bond or —CH$_2$—.

Examples of radicals R$^7$ in addition to the specific radicals listed are COOCH$_3$, COOC$_2$H$_5$, COOC$_3$H$_7$, COOC$_4$H$_9$, COOC$_8$H$_{17}$, CONH$_2$, CONHCH$_3$, CONHC$_2$H$_5$, CONHC$_3$H$_7$, CONHC$_4$H$_9$, CONHC$_6$H$_{13}$, CONHC$_8$H$_{17}$, CON(CH$_3$)$_2$, CON(C$_2$H$_5$)$_2$, CON(C$_3$H$_7$)$_2$, CON(C$_4$H$_9$)$_2$, CON(C$_6$H$_{13}$)$_2$, CON(C$_8$H$_{17}$)$_2$, OCH$_3$, OC$_2$H$_5$, OC$_3$H$_7$ and C$_4$H$_9$.

R$^7$ is preferably COOH, CONH$_2$, COOCH$_3$ or COOC$_2$H$_5$, but in particular hydrogen.

Examples of radicals R$^8$ is addition to hydrogen are C$_1$–C$_4$-alkyl and benzyl.

Compounds of the general formula (I) can be prepared by reacting a tetramethylolacetylenediurea (II) with a 4-amino-2,2,6,6-tetraalkylpiperidine by a method similar to that described in French Pat. No. 2,291,203.

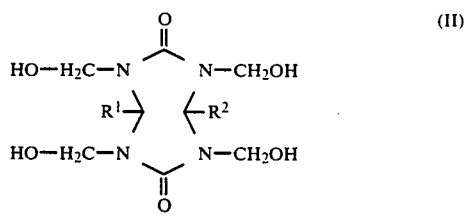

Compounds of the formula I may furthermore be prepared by a single-vessel process by reacting glycoluril, formaldehyde and a 4-amino-2,2,6,6-tetraalkylpiperidine by methods similar to that described in J. Org. Chem. 50 (1985), 60.

The compounds of the formula (I) where X—R$^7$ is H may be converted to the compounds in which X—R$^7$ is CH$_3$ by processes known from the literature, for example by reductive amination.

Compounds of the formula (III)

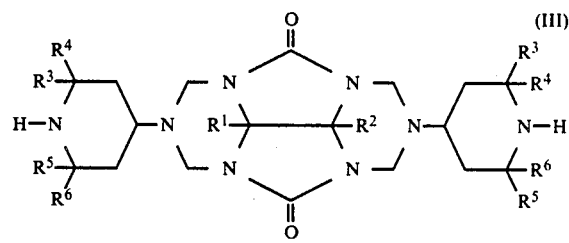

may furthermore be converted to compounds of the formula (I) where X—R$^7$ is not H by alkylation or acylation by processes known from the literature.

The compounds according to the invention may be in the form of the free bases or of the salts. Examples of suitable anions are those derived from inorganic acids and in particular organic carboxylic acids and organic sulfonic acids.

The novel compounds possess extremely good stabilizing properties, have no natural color, are highly compatible with organic polymers and have a low vapor pressure.

Examples of inorganic anions are chloride, bromide, sulfate, methosulfate, tetrafluoroborate, phosphate and thiocyanate.

Examples of carboxylic acid anions are formate, acetate, propionate, hexanoate, cyclohexanoate, lactate, stearate, dodecylbenzoate, benzoate, acrylate, methacrylate, citrate, malonate and succinate and anions of polycarboxylic acids containing up to 3000 COOH groups.

Examples of sulfonic acid anions are benzene sulfonate and tosylate.

The compounds according to the invention are useful for stabilizing organic material, especially plastics, toward degradation by light and heat. They are added to the plastics to be stabilized in a concentration of from 0.01 to 5, preferably from 0.02 to 1, % by weight, before, during or after polymer formation.

Mixing of the novel compounds with the plastics to be stabilized can be carried out using any conventional apparatus and method for mixing stabilizers or other additives into polymers.

The plastics stabilized by one of the novel compounds can, if required, contain further additives, for example antioxidants, light stabilizers, metal deactivators, antistatic agents, flame retardants, pigments and fillers.

Antioxidants and light stabilizers which can be added to the plastics in addition to the novel compounds are, for example, compounds based on sterically hindered phenols or costabilizers containing sulfur or phosphorus.

Examples of phenolic antioxidants of this type are 2,6-di-tert.-butyl-4-methylphenol, n-octadecyl-β-(3,5-di-tert.-butyl-4-hydroxyphenyl)-propionate, 1,1,3-tris-(2-methyl-4-hydroxy-5-tert.-butylphenyl)-butane, 1,3,5-trimethyl-2,4,6-tris-(3,5-di-tert.-butyl-4-hydroxybenzyl)benzene, 1,3,5-tris-(3,5-di-tert.-butyl-4-hydroxybenzyl)isocyanurate, 1,3,5-tris-[β-(3,5-di-tert.-butyl-4-hydroxyphenyl)-propionyloxyethyl]isocyanurate, 1,3,5-tris-(2,6-dimethyl-3-hydroxy-4-tert.-butylbenzyl)isocyanurate, pentaerythritol tetrakis-[β-(3,5-di-tert.-butyl-4-hydroxyphenyl)-propionate], etc.

Examples of phosphorus-containing antioxidants are tris(nonylphenyl)phosphite, distearyl pentaerythritol diphosphate, tris-(2,4-di-tert.-butylphenyl)phosphite, tris-(2-tert.-butyl-4-methylphenyl)phosphite, bis-(2,4-di-tert.-butylphenyl)pentaerythritol diphosphite, tetrakis-(2,4-di-tert.-butylphenyl)4,4'-biphenylene diphosphite, etc.

Examples of sulfur-containing antioxidants are dilauryl thiodipropionate, dimyristyl thiodipropionate, distearyl thiodipropionate, pentaerythritol tetrakis-(β-laurylthiopropionate), pentaerythritol tetrakis-(β-hexylthiopropionate), etc.

Other antioxidants and light stabilizers which can be used together with the novel compounds are, for example, 2-(2'-hydroxyphenyl)-benzotriazoles, 2-hydroxybenzophenones, aryl esters of hydroxybenzoic acids, α-cyanocinnamic acid derivatives, nickel compounds and oxalic acid dianilides.

Examples of organic polymers which can be stabilized using the novel compounds are:

polymers of mono- and diolefins, such as low density or high density polyethylene, linear low density polyethylene, polypropylene, polyisobutylene, polybut-1-ene, polyisoprene or polybutadiene, and copolymers of mono- or diolefins or blends of the stated polymers;

copolymers of mono- or diolefins with other vinyl monomers, such as ethylene/alkyl acrylate copolymers, ethylene/alkyl methacrylate copolymers, ethylene/vinyl acetate copolymers or ethylene/acrylic acid copolymers;

polystyrene;

copolymers of styrene or α-methylstyrene with dienes or acrylyl derivatives, such as styrene/butadiene, styrene/acrylonitrile, styrene/ethyl methacrylate, styrene/butadiene/ethyl acrylate or styrene/acrylonitrile/methacrylate;

ABS, MBS and similar polymers;

halogen-containing polymers, eg. polyvinyl chloride, polyvinyl fluoride, polyvinylidene fluoride and their copolymers; polymers which are derived from α,β-unsaturated acids and their derivatives, such as polyacrylates and polymethacrylates, polyacrylamides and polyacrylonitriles;

polymers which are derived from unsaturated alcohols and amines and their acrylyl derivatives or acetals, such as polyvinyl alcohol or polyvinyl acetate;

polyurethanes, nylons, polyureas, polyesters, polycarbonates, polysulfones, polyethersulfones and polyether ketones.

Other organic polymers which can be stabilized with the compounds according to the invention are industrial coatings. Particularly noteworthy among these are baking finishes, including automotive finishes, preferably two-coat finishes.

Here too, the antioxidants and light stabilizers stated above may be used in addition.

The solid compounds according to the invention can be added to the coating in solid or dissolved form, while liquid compounds according to the invention can be added as such. Their good solubility in coating systems is particularly advantageous.

The novel compounds are preferably used in polyolefins, preferably ethylene and propylene polymers.

Of particular importance are compounds of the general formula Ia

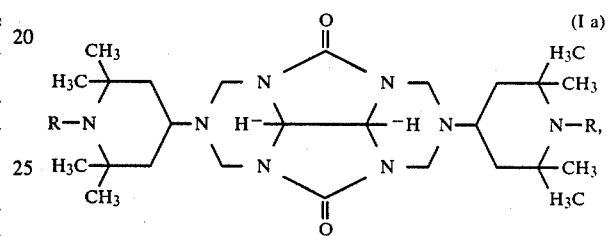

where R is hydrogen, methyl, ethyl, propyl, butyl, allyl, hydroxymethyl, acetyl, benzoyl or benzyl.

EXAMPLE 1a 15.6 g (0.1 mole) of 4-amino-2,2,6,6-tetramethylpiperidine and 13.1 g (0.05 mole) of tetramethylolacetylenediurea are added to 100 ml of n-butanol, and the mixture is refluxed for 6 hours. After the solvent has been distilled off, 23.2 g (92%) of a colorless solid of melting point 250°–252° C. are obtained.

Calculated: C 62.2; H 9.2; N 22.3; Found: C 62.6; H 9.1; N 21.7

Impurities are removed by boiling thoroughly with water, after which the melting point is found to have increased to 280°–283° C.

EXAMPLE 1b 65.7 kg of 4-amino-2,2,6,6-tetramethylpiperidine and 104.8 kg of a 50% strength aqueous solution of tetramethylolacetylenediurea are added to 300 l of water. The mixture is heated at 80°–90° C. for 2 hours and left to cool at room temperature, and the product is filtered off under suction, washed with water and dried under reduced pressure. 89.5 kg (90%) of a colorless solid of melting point 280°–283° C. are obtained.

Calculated: C 62.2; H 9.2; N 22.3; Found: C 62.2; H 9.4; N 22.3

EXAMPLE 1c 56.8 g (0.4 mole) of acetylenediurea, 160 g (1.6 moles) of 30% strength aqueous formaldehyde solution and 124.8 g (0.8 mole) of 4-amino-2,2,6,6-tetramethylpiperidine in 250 ml of water are heated at 90°–95° C. for 2 hours. The mixture is cooled, after which the product is filtered off under suction, washed with water and dried to give 186.9 g (93%) of a colorless solid, which the melting point and IR and elemental analysis show to be identical to the product of Example 1a.

EXAMPLE 2

26.2 g (0.05 mole) of a 50% strength aqueous solution of tetramethylolacetylenediurea are added to 17.0 g (0.1 mole) of 4-amino-1,2,2,6,6-pentamethylpiperidine in 200 ml of water, and the mixture is kept at 80° C. for 2 hours. The mixture is filtered under suction at room temperature to give 23.8 g (90%) of colorless crystals of melting point 257°–261° C., which are further purified by recrystallization from ethanol.

Calculated: C 63.4; H 9.4; O 6.0; N 21.1; Found: C 63.1; H 9.4; O 6.0; N 21.1

EXAMPLE 3

4.95 g (0.019 mole) of tetramethylolacetylenediurea and 20.0 g (0.057 mole) of about 70% strength 4-amino-1-benzyl-2,2,6,6-tetramethylpiperidine in 60 ml of n-butanol are refluxed for 6.5 hours. The precipitate which separates out is filtered off under suction at room temperature, washed with n-butanol and recrystallized from ethanol. The dibenzyl compound is isolated as colorless crystals of melting point 283° C.

Calculated: C 70.4; H 8.5; O 4.7; N 16.4; Found: C 70.1; H 8.5; O 4.8; N 16.5

EXAMPLE 4

25 g (0.05 mole) of the product from Example 1 and 40.8 g (0.40 mole) of acetic anhydride in 200 ml of xylene are boiled for 5 hours. The precipitate which separates out is filtered off under suction at room temperature, dried, and dissolved in water. The aqueous solution is rendered alkaline with sodium hydroxide solution, and the precipitate is filtered off under suction, dried and recrystallized from isopropanol. The diacetyl compound is obtained as a colorless solid of melting point 280° C.

Calculated: C 61.4; H 8.5; O 10.9; N 19.1; Found: C 61.3; H 8.7; O 11.1; N 19.2

EXAMPLE 5

8.5 g (50 millimole) of 1,5-dimethyl-2,4,6,8-tetraazabicyclo[3.3.0]octane-3,7-dione, 20 ml of 30% strength aqueous formaldehyde solution and 15.5 g (100 millimoles) of 4-amino-2,2,6,6-tetramethylpiperidine in 200 ml of isopropanol are boiled for 7 hours. The solvent is distilled off, and the residue is boiled thoroughly with water. After recrystallization from ethylene glycol dimethyl ether, the product is isolated as colorless crystals of melting point 279°–281° C.

Calculated: C 63.4; H 9.4; O 6.0; N 21.1; Found: C 63.2; H 9.4; O 6.4; N 21.2

EXAMPLE 6

16.0 g (0.08 mole) of 1,5-dimethyl-2,4,6,8-tetraazabicyclo[3.3.0]octane-3-thion-7-one, 32 ml of 30% strength formaldehyde solution and 24.8 g (0.16 mole) of 4-amino-2,2,6,6-tetramethylpiperidine in 200 ml of isopropanol are heated at the boil for 7 hours. The solvent is distilled off, the residue is suspended in water, and the product is filtered off under suction, dried, and recrystallized from ethylene glycol dimethyl ether. The product is isolated as a colorless solid of melting point 243°–245° C.

Calculated: C 61.5; H 9.2; O 2.9; N 20.5; S 5.9; Found: C 61.3; H 9.4; O 3.1; N 20.4; S 6.0

EXAMPLE 7

14.7 g (0.05 mole) of 1,5-diphenyl-2,4,6,8-tetraazabicyclo[3.3.0]octane-3,7-dione, 20 ml of 30% strength formaldehyde solution and 15.5 g (0.1 mole) of 4-amino-2,2,6,6-tetramethylpiperidine in 200 ml of isopropanol and 150 ml of dimethyl sulfoxide are heated at the boil for 7 hours. The product is filtered off under suction at room temperature, stirred up in 250 ml of dichloromethane and filtered off under suction again. 23.2 g (71%) of product are obtained in the form of a colorless solid of melting point <310° C.

Calculated: C 69.7; H 8.2; O 4.9; N 17.1; Found: C 69.5; H 8.3; O 5.0; N 17.1

EXAMPLE 8

16.3 g (0.05 mole) of 1,5-diphenyl-2,4,6,8-tetraazabicyclo[3.3.0]octane-3,7-dithione, 20 ml of 30% strength aqueous formaldehyde solution and 15.5 g (0.1 mole) of 4-amino-2,2,6,6-tetramethylpiperidine in 150 ml of dimethyl sulfoxide are heated at 80° C. for 7 hours and at 150° C. for 10 hours. The product is filtered off under suction at room temperature and washed with water. It is colorless and has a melting point of 255°–256° C.

Calculated: C 66.5; H 7.9; N 16.3; S 9.3; Found: C 66.6; H 7.8; N 16.0; S 9.1

EXAMPLE 9

Salt of the compound of Example 1 and 1 mole of adipic acid.

5.0 g of the product from Example 1 and 1.64 g of adipic acid are dissolved in 150 ml of methanol, and the solution is evaporated to dryness to give the salt, which crystallizes with 2 molecules of methanol and is in the form of a colorless solid of melting point 230°–232° C.

EXAMPLE 10

Salt of the compound of Example 1 with 2 moles of 2,5-dimethylfuran-3-carboxylic acid.

5.0 g of the product from Example 1 and 2.78 g of 2,5-dimethylfuran-3-carboxylic acid are reacted similarly to Example 9. The salt which crystallizes with 2 molecules of methanol is obtained as a colorless solid of melting point 258°–260° C.

Calculated: C 59.6; H 8.3; O 18.9; N 13.2; Found: C 59.6; H 8.34; O 18.0; N 13.7

EXAMPLE 11

Salt of the compound of Example 1 with 2 moles of 3-(3,5-di-tert.-butyl-4-hydroxyphenyl)-propionic acid.

5 g of the product from Example 1 and 5.7 g of 3-(3,5-di-tert.-butyl-4-hydroxyphenyl)-propionic acid are reacted similarly to Example 9. The salt which crystallizes with 4 molecules of methanol is obtained as a colorless solid of melting point 208°–210° C.

Calculated: C 64.7; H 9.4; O 16.1; N 9.4; Found: C 64.4; H 9.4; O 15.9; N 9.8

USE EXAMPLES

1. Stabilization of polyethylene with the compound of Example 1
   (a) 0.25 part of the compound from Example 1 is incorporated into 100 parts of low density polyethylene (1840 D from BASF) by extruding twice at 180° C., and the polyethylene is then pressed to give 200 μm thick sheets. After storage for 14 days in the dark at 25° C., the surface of the sheets does not have any coating.
(b) The weathering stability of the sheets produced as described in (a) is tested in a QUV accelerated weathering test apparatus. The aging is determined by measuring the CO number after certain time intervals. Embrittlement is considered to have been reached when the CO number is 10. The test results are summarized in Table 1.

Specimens containing the compounds from Examples 1 and 2 and the stabilizer of formula IV are prepared similarly to Example 1(a) and tested similarly to Example 1(b). The results are summarized in Table 1.

TABLE 1

IV: HN–⟨ ⟩–O–C(=O)–(CH$_2$)$_8$–C(=O)–O–⟨ ⟩–NH

CO numbers on exposure in a QUV accelerated weathering test apparatus (polyethylene)

| Compound | Exposure time in h | | | |
|---|---|---|---|---|
| | 0 | 1000 | 2000 | 3000 |
| Example 1 | 0.33 | 0.32 | 0.14 | 0.15 |
| Example 2 | 0.08 | 0.07 | 0.11 | 0.15 |
| Stabilizer of the formula IV | not compatible | | | |

2. Stabilization of polypropylene
  (a) 0.25 part of a compound of the appropriate example is incorporated into 100 parts of polypropylene (1320 H from BASF) by extruding twice at 220° C., and the polypropylene is pressed to give 200 μm thick sheets. After storage for 14 days in the dark at 25° C., the surface of the sheets has no coating.
  (b) The weathering stability of the sheets produced as described in (a) is tested in a QUV accelerated weathering test apparatus. The aging is determined by measuring the CO number after certain time intervals. The onset of embrittlement is determined mechanically. The test results are summarized in Table 2.

TABLE 2

CO numbers on exposure in a QUV accelerated weathering test apparatus (polypropylene)

| Compound | Exposure time in h | | | |
|---|---|---|---|---|
| | 0 | 1000 | 2000 | 3000 |
| Example 1 | 3.70 | 4.34 | 46 | brittle |
| Example 2 | 3.40 | 3.60 | 4.01 | 6.19 |
| Stabilizer of the formula IV | 1.65 | 1.70 | brittle | |

We claim:
1. A compound of formula (I)

wherein:
n is from 1 to 70;
$R^1$ and $R^2$ are each independently hydrogen, $C_1$–$C_6$-alkyl, $C_7$–$C_{10}$ phenylalkyl, phenyl, tolyl or a $C_{2-5}$ carboxylic ester group; or
$R^1$ and $R^2$ together form a tetramethylene or pentamethylene group;
$R^3$, $R^4$, $R^5$ and $R^6$ are each $C_{1-4}$ alkyl, or any two adjacent groups $R^3$, $R^4$, $R^5$ and $R^6$ form a tetramethylene or pentamethylene group;
each X, independent of all other groups X, is a direct bond or a bridge member which is one member selected from the group consisting of $(CH_2)_p$, $(CH_2)_p CH=CH$, $(CH_2)_p C\equiv C$, $(CH_2)_m$–⟨C$_6$H$_4$⟩–, $(CH_2)_m$–⟨C$_6$H$_{10}$⟩–H, $(CH_2)_m$–⟨C$_5$H$_8$⟩–H, –$(CH_2)_m$–⟨C$_6$H$_4$⟩–$(CH_2)_m$, $(CH_2)_2O$, $(CH_2)_2O(CH_2)_2$, $(CH_2)_3O(CH_2)_2$,

CH(CH$_3$)–CH$_2$–O(CH$_2$)$_2$, (CH$_2$)$_2$OCH(CH$_3$)–CH$_2$,

CH(CH$_3$)–CH$_2$OCH(CH$_3$)–CH$_2$, –C(=O)–(CH$_2$)$_m$–, –C(=O)–(CH$_2$)$_m$–O–,

–C(=O)–(CH$_2$)$_m$–O–(CH$_2$)$_m$–C(=O)–, –SO$_2$–⟨Ar⟩,

–C(=O)–⟨Ar⟩, –C(=O)–(CH$_2$)$_m$–C$_6$H$_4$,

–C(=O)–⟨Ar⟩–C(=O)– and –C(=O)–(CH$_2$)$_p$–C(=O)– where p is an integer of from 1 to 20 and m is an integer of from 0 to 4;
Y and Z are each independently oxygen, sulfur or $NR^8$;

$R^7$ is hydrogen, chlorine, bromine, hydroxyl, $C_{1-4}$ alkoxy, $C_{1-4}$ alkyl, allyl, hydroxymethyl, acetyl, benzoyl, benzyl, carboxyl, a $C_{2-9}$ carboxylic ester group, an unsubstituted carbamyl, or a $C_{1-8}$-mono- or di-substituted carbamyl;

$R^8$ is hydrogen, benzyl or $C_{1-4}$-alkyl;

or an ammonium salt of said compound of formula (I).

2. The compound of claim 1, wherein n is an integer of from 1 to 20.

3. The compound of claim 1, wherein n is 1.

4. The compound of claim 1, wherein $R^1$ and $R^2$ are each hydrogen.

5. The compound of claim 3, wherein $R^1$ and $R^2$ are each hydrogen.

6. The compound of claim 3, wherein $R^1$ or $R^2$ is methyl or phenyl, or $R^1$ and $R^2$ are each methyl or phenyl.

7. The compound of claim 3, wherein $R^3$, $R^4$, $R^5$ and $R^6$ are each methyl, and $X-R^7$ is hydrogen.

8. The compound of claim 3, wherein $R^3$, $R^4$, $R^5$, $R^6$ and $X-R^7$ are each methyl.

9. The compound of claim 1, said compound having formula (Ia)

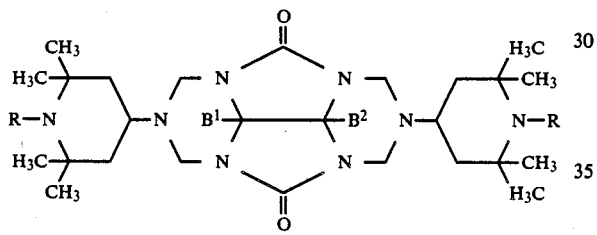

wherein:

$B^1$ and $B^2$ are each independently hydrogen, methyl or phenyl; and

R is hydrogen, methyl, ethyl, propyl, butyl, allyl, hydroxymethyl, acetyl, benzoyl or benzyl.

10. The compound of claim 9, wherein R is hydrogen or methyl.

11. The compound of claim 1, wherein $R^1$ and $R^2$ are each independently hydrogen, methyl, ethyl, propyl, butyl, pentyl, hexyl, benzyl, phenylethyl, phenylpropyl, phenylbutyl, methylbenzyl, phenyl, tolyl, carbomethoxy, carboethoxy, carbopropoxy, or carbobutoxy.

12. The compound of claim 1, wherein X is one member selected from the group consisting of $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$, $-(CH_2)_{10}-$, $-(CH_2)_{11}-$, $-(CH_2)_{12}-$, $-(CH_2)_{13}-$, $-(CH_2)_{14}-$, $-(CH_2)_{16}-$, $-(CH_2)_{17}-$, $-(CH_2)_{20}-$,

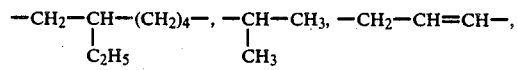

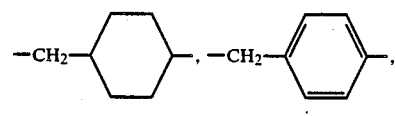

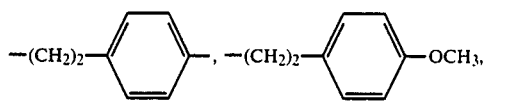

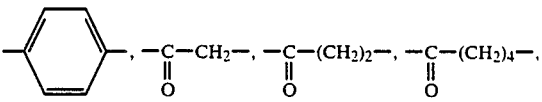

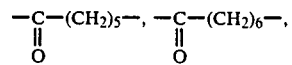

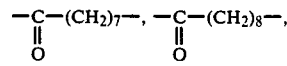

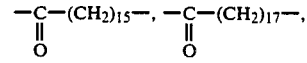

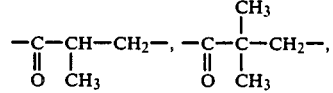

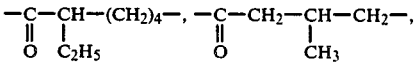

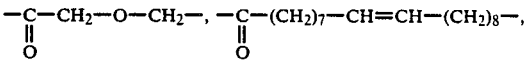

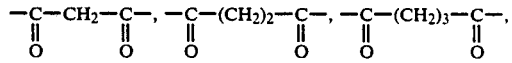

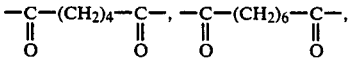

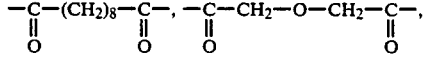

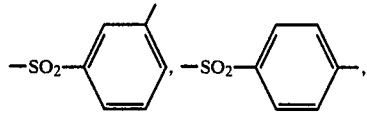

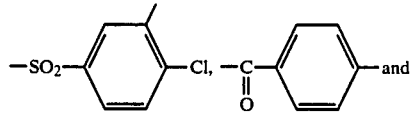

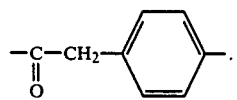

13. The compound of claim 1, wherein X is a direct bond or $-CH_2-$.

14. The compound of claim 1, wherein $R^7$ is one member selected from the group consisting of $COOCH_3$, $COOC_2H_5$, $COOC_3H_7$, $COOC_4H_9$, $COOC_8H_{17}$, $CONH_2$, $CONHCH_3$, $CONHC_2H_5$, $CONHC_3H_7$, $CONHC_4H_9$, $CONHC_6H_{13}$, $CONHC_8H_{17}$, $CON(CH_3)_2$, $CON(C_2H_5)_2$, $CON(C_3H_7)_2$, $CON(C_4H_9)_2$, $CON(C_6H_{13})_2$, $CON(C_8H_{17})_2$, $OCH_3$, $OC_2H_5$, $OC_3H_7$ and $C_4H_9$.

15. The compound of claim 1, wherein $R^7$ is COOH, $CONH_2$, $COOCH_3$, $COOC_2H_5$ or hydrogen.

* * * * *